US011291629B2

(12) United States Patent
Takada

(10) Patent No.: US 11,291,629 B2
(45) Date of Patent: Apr. 5, 2022

(54) MUCOADHESIVE ORAL PREPARATION

(71) Applicant: BIOSERENTACH CO., LTD., Kyoto (JP)

(72) Inventor: Kanji Takada, Kyoto (JP)

(73) Assignee: BIOSERENTACH CO., LTD., Kyoto (JP)

(*) Notice: Subject to any disclaimer, the term of this patent is extended or adjusted under 35 U.S.C. 154(b) by 0 days.

(21) Appl. No.: 16/624,423

(22) PCT Filed: Jun. 22, 2018

(86) PCT No.: PCT/JP2018/023851
§ 371 (c)(1),
(2) Date: Dec. 19, 2019

(87) PCT Pub. No.: WO2019/004088
PCT Pub. Date: Jan. 3, 2019

(65) Prior Publication Data
US 2020/0129420 A1    Apr. 30, 2020

(30) Foreign Application Priority Data

Jun. 27, 2017  (JP) .............................. JP2017-125572

(51) Int. Cl.
| A61K 9/00 | (2006.01) |
| A61K 9/20 | (2006.01) |
| A61K 9/70 | (2006.01) |
| A61K 31/55 | (2006.01) |
| A61K 31/573 | (2006.01) |
| A61K 31/58 | (2006.01) |
| A61K 38/28 | (2006.01) |
| A61K 47/38 | (2006.01) |

(52) U.S. Cl.
CPC ............ *A61K 9/006* (2013.01); *A61K 9/2027* (2013.01); *A61K 9/2054* (2013.01); *A61K 9/7007* (2013.01); *A61K 31/55* (2013.01); *A61K 31/573* (2013.01); *A61K 31/58* (2013.01); *A61K 38/28* (2013.01); *A61K 47/38* (2013.01)

(58) Field of Classification Search
CPC ........ A61K 9/006; A61K 38/28; A61K 31/55; A61K 31/573; A61K 47/38; A61K 9/7007; A61K 9/2054; A61K 9/2027; A61K 31/58; A61K 9/2072; A61K 9/2086; A61K 45/00; A61K 47/14; A61K 47/26; A61K 47/32; A61P 3/10; A61P 5/38; A61P 25/20; A61P 43/00
See application file for complete search history.

(56) References Cited

U.S. PATENT DOCUMENTS

| 6,242,004 B1 | 6/2001 | Rault | |
| 7,097,851 B1* | 8/2006 | Takada | ................. A61K 9/4808 424/435 |
| 2015/0174076 A1* | 6/2015 | Harris | .................... A61K 9/006 424/489 |

FOREIGN PATENT DOCUMENTS

| JP | 9-104640 | 4/1997 |
| JP | 10-298063 | 11/1998 |
| JP | 2001-354550 | 12/2001 |
| JP | 2001-354593 | 12/2001 |
| JP | 2002-531394 | 9/2002 |
| JP | 2005-295854 | 10/2005 |
| JP | 2006-111558 | 4/2006 |
| JP | 4497725 | 4/2010 |
| JP | 2010-235486 | 10/2010 |
| JP | 2015-519403 | 7/2015 |
| WO | 00/32172 | 6/2000 |
| WO | 2012/080471 | 6/2012 |
| WO | 2013/188819 | 12/2013 |

OTHER PUBLICATIONS

English-language translation International Preliminary Report on Patentability dated Dec. 31, 2019 in International (PCT) Application No. PCT/JP2018/023851.
International Search Report (ISR) dated Aug. 7, 2018 in International (PCT) Application No. PCT/JP2018/023851.
K. Whitehead, et al., "Oral delivery of macromolecules using intestinal patches: applications for insulin delivery", Journal of Controlled Release, vol. 98, pp. 37-45, 2004.
Kanji Takada, Fragrance Journal, vol. 32, No. 1, pp. 96-102, 2004.
S. Bahadur et al., "Physicochemical characterization and evaluation of mucoadhesive tablets of omeprazole for local action". Journal of Pharmaceutical Sciences and Research, vol. 1, No. 4, pp. 116-122, 2009.

* cited by examiner

*Primary Examiner* — Snigdha Maewall
(74) *Attorney, Agent, or Firm* — Wenderoth, Lind & Ponack, L.L.P.

(57) ABSTRACT

An object of the invention is to provide a mucoadhesive oral preparation having high drug absorption rate and rapid drug release rate. The means for solving the problem is a mucoadhesive oral preparation having (a) a basal layer substantially consisting of a water-insoluble material, (b) a drug layer locating above the basal layer and containing a drug but not containing mucoadhesive material, and (c) an adhesive portion locating on a portion of the surface of the drug layer side of the oral formulation and containing mucoadhesive material.

7 Claims, 3 Drawing Sheets

MUCOADHESIVE ORAL PREPARATION

TECHNICAL FIELD

The present invention relates to mucoadhesive oral preparation, especially mucoadhesive oral preparation of which drug absorption efficiency is improved after oral administration.

BACKGROUND ART

The passive transport mechanism due to the simple diffusion of drug molecules is the dominant mechanism on the absorption of drugs. Gastrointestinal mucoadhesive patch system (GI-MAPS) is described in Patent Documents 1 and 2 as a drug delivery system (DDS) to improve the extent of absorption of drugs from the gastrointestinal tract of which absorption mechanism is due to the simple diffusion mechanism. Furthermore, Patent Documents 1 and 3 describe mucoadhesive tablet and devices.

GI-MAPS is basically a film preparation composed of three layers structure, and is composed of three-part layers, namely, (a) a bottom layer made of water-insoluble material (basal layer), (b) surface layer made of enteric polymer material film for determining the dissolution site in the gastrointestinal tract, and (c) intermediate layer (or drug layer) composed of adhesive material, absorption enhancer, stabilizing agent and drug. However, mucoadhesive material, which is formulated with drug in the intermediate layer or applied whole over the surface layer facing to the intermediate layer, is a water-soluble adhesive gel-forming macromolecular material (polymer material) of which typical example is a Polycarbophil. Therefore, it is difficult to obtain high absorption rate of drug, because drug molecules are kept within the mucoadhesive polymer material or need long time to diffuse through the gel due to the existence of mucoadhesive polymer material applied under the surface layer. This is because adhesive polymer materials like Polycarbophil are practically used as the main component of oral sustained-release preparation.

As GI-MAPS is a DDS to improve the extent of absorption of poorly-absorbable drugs by adhering to the small intestinal mucosa, lag-time of more than 1 hour occurs before pharmacological activity is obtained after intake. Therefore, even if GI-MAPS is applied to the drugs which need the rapid appearance of pharmacological activity after intake, such as sleep-inducing drugs and anti-diabetic drugs of which pharmacological activity is hypoglycemia, efficacy is low.

In non-patent documents 1 and 3, DDSs for oral administration of insulin are described. It is a thin or protruding tablet in which insulin, absorption enhancer and mucoadhesive gel-forming polymer material are formulated. After intake, although it attached to the small intestinal mucosa by the function of the gel-forming polymer material, high extent of absorption was not obtained, because the diffusion rate of drug molecules within the gel was slow.

PRIOR ART DOCUMENTS

Patent Document

Patent document1: JP 2002-531394 A
Patent document2: JP 2006-111558 A
Patent document3: JP 2015-519403 A

Non-Patent Document

Non-patent document1: K. Whitehead, Z. Shen and S. Mitragotri, "Oral delivery of macromolecules using intestinal patches: applications for insulin delivery", J. Control. Rel., 98, 37-45, 2004

DISCLOSURE OF THE INVENTION

Problem to be Solved by the Invention

The present invention is intended to solve the above-mentioned problems, and the object of the present invention is to provide an oral mucoadhesive preparation having high extent of drug absorption and high drug release rate.

The present invention provides a mucoadhesive oral preparation having (a) a basal layer substantially consisting of water-insoluble material, (b) a drug layer locating above the basal layer and containing a drug but not containing mucoadhesive material, and (c) an adhesive portion locating on a portion of the surface of the drug layer side of the oral formulation and containing mucoadhesive material.

In one embodiment, the adhesive portion locates on the outer periphery of the surface of the drug layer side.

In one embodiment, the adhesive portion locates on the outer periphery on the surface of the basal layer, and the drug layer locates in the central portion on the surface of the basal layer.

In one embodiment, the adhesive portion is substantially consisting of mucosal adherent material.

In one embodiment, the water-insoluble material is at least one selected from the group consisting of ethylcellulose, cellulose acetate, chitin, chitosan, aminoalkyl methacrylate copolymer RS, carboxymethylethylcellulose, crystalline cellulose, dimethylaminoethyl methacrylate-methyl methacrylate copolymer, hydroxypropyl starch, hydroxypropyl methylcellulose phthalate, polyvinylacetal diethylaminoacetate, cellulose acetate phthalate, stearic acid, magnesium stearate, acetylglycerol fatty acid ester, magnesium silicate, cholesterol and water-insoluble glycerol fatty acid esters.

In one embodiment, the mucoadhesive material is at least one selected from the group consisting of carboxyvinyl polymer, polyacrylic acid and its salts, alginic acid and its salts and propylene glycol alginate ester.

In one embodiment, any of the above mentioned oral preparations have a dosage form of tablets or film preparation.

In one embodiment, the drugs are at least one selected from the group composed of insulin and insulin derivatives, GLP-1 receptor agonists, sleep inductors, steroids, and anti-inflammatory drug, and the dosage form is tablet.

In one embodiment, the drugs are at least one selected from the group consisting of sleep inducers, steroids, and anti-inflammatory drug, and the dosage form is a film agent.

Effect of the Invention

According to the present invention on mucoadhesive oral preparation, it becomes possible to deliver drugs such as cardiovascular drugs to the systemic circulation with high absorption rate and high extent of absorption.

It is a cross-sectional view schematically showing the structure of the mucoadhesive oral preparation of one embodiment of the present invention.

FIG. 2

It is a partial perspective view schematically showing the structure of mucoadhesive oral preparation of another embodiment of the present invention.

FIG. 3

It is a plan view schematically showing the structure of the mucoadhesive oral preparation of the present invention prepared as Example 16.

FIG. 4

It is a plan view schematically showing the structure of mucoadhesive oral preparation of another embodiment of the present invention.

FIG. 5

It is a graph showing the results comparing the permeability rate of drug from the film preparation of Example 10 and Comparative Example 4 to the receptor side using Franz cell for in vitro permeation experiments.

FIG. 6

It is a graph showing the results comparing the permeability rate of drug from the preparation of Example 12 and Comparative Example 5 to the receptor side using Franz cell for in vitro permeation experiments.

EMBODIMENT FOR CARRYING OUT THE INVENTION

Figure 1:
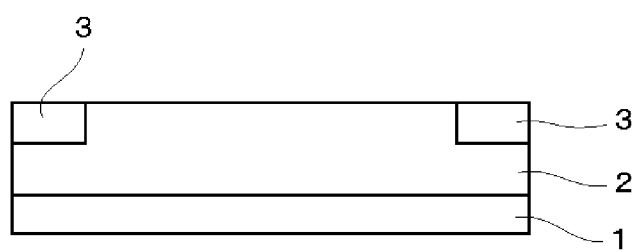
FIG. 1

FIG. 1 is a cross-sectional view schematically showing the one embodiment of the present invention on mucoadhesive oral preparation. The outer form of the mucoadhesive oral preparation of FIG. 1 is, for example, a disk-shaped. The outer shape of the oral preparation may be a disk shape of which bottom surface is oval. This mucoadhesive oral preparation has (a) basal layer 1, (b) drug layer 2 located on the surface of the basal layer, and (c) adhesive portion 3 located on a part of the surface of the drug layer side of oral preparation.

Drug layer 2 does not need to be in contact with the surface of the basal layer 1. Intermediate layer may be present between the basal layer 1 and the drug layer 2. Although intermediate layer is preferably water-insoluble, it may be made of water-soluble material. Specific examples of the intermediate layer include layers containing mucoadhesive materials. In oral preparation, when the direction of the mucoadhesive surface is assumed to be upward, the drug layer 2 may be located above the basal layer 1. Drug layer 2 preferably has an exposed surface at the upper surface of the oral preparation. In other case, an enteric coating membrane exists on the drug layer 2.

The position of the adhesive portion 3 is preferably the outer peripheral portion of the surface of the drug layer side of the oral preparation. In doing so, it becomes easy for the drug layer to adhere to the surface of the mucosa. However, as the effect of increasing absorption efficiency by increasing the absorption rate of the drug is achieved by formulating drug separately from the mucoadhesive material, the position of the adhesion portion 3 is not limited thereto, and it may be positioned in the part of surface of the drug layer side of the oral preparation.

Figure 2:
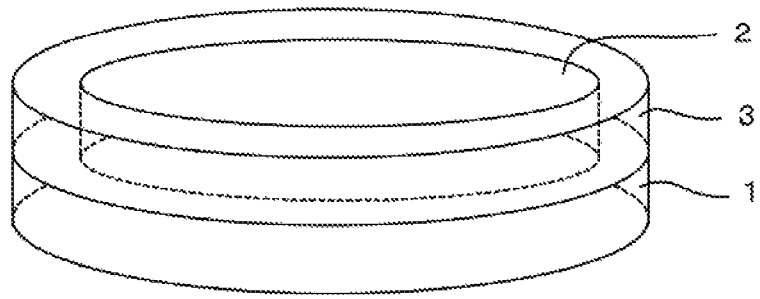

FIG. 2 is a partial perspective view schematically showing the structure of mucoadhesive oral preparation in another embodiment of the present invention. In this mucoadhesive oral preparation, the adhesion portion 3 is located on the outer periphery on the surface of the basal layer 1, and the drug layer 2 is located in the central portion on the surface of the basal layer 1.

Figure 3:
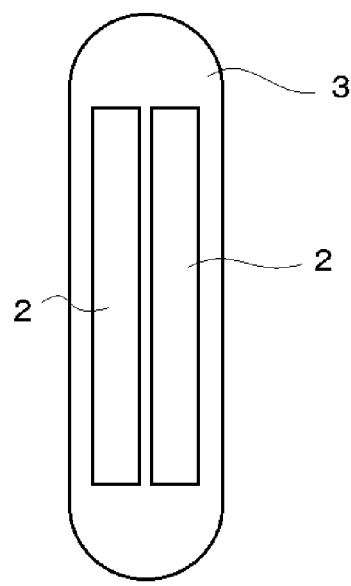

FIG. 3 is a plan view schematically showing the structure of the mucoadhesive oral preparation of the present invention prepared as Example 16. The mucoadhesive oral preparation has a basal layer being a water-insoluble coating membrane (hidden), a drug layer 2 located above the basal layer, and the adhesive portion 3 located on a part of the surface of the drug layer side of the oral preparation.

(a) Basal Layer

Basal layer has a function to form barrier layer which protect drug from the degradation like hydrolysis by preventing the permeation of saliva and gastrointestinal juice inside the oral preparation of the present invention after adhering to the mucosa. As water-insoluble materials to form the basal layer, a material having stability in vivo, especially stability in the digestive organs is used.

Typical water-insoluble materials in pharmaceutical additives for oral preparation are cellulose acetate, ethylcellulose, chitin, chitosan, aminoalkyl methacrylate copolymer RS, carboxymethylethylcellulose, crystalline cellulose, dimethylaminoethylmethacrylate methylmethacrylate copolymer, hydroxypropyl starch, hydroxypropyl methylcellulose phthalate, polyvinyl acetal diethylaminoacetate, and water-insoluble polymer excipients such as cellulose phthalate acetate, stearic acid, magnesium stearate, and higher fatty acids such as acetylglycerol fatty acid esters, magnesium silicate, cholesterol, and water-insoluble glycerol fatty acid esters and the like. However, it is not limited to these water-insoluble materials. The form of the basal layer may be thin layer compressed with raw material powder, a film molded from the raw material, or a coated membrane followed coating and drying of raw material solution.

Basal layer, for example, may be formed by filling the water-insoluble material as the lowest layer in the mortar in the case of tableting. Alternatively, basal layer may be formed once forming a tablet having an adhesive portion and a drug layer, then a coating solution in which water-insoluble materials such as cellulose acetate or ethyl cellulose is dissolved is applied to the bottom surface of the tablet.

(b) Adhesive Portion

Adhesive portion has a function of adhering the oral preparation of the present invention to the surface of the mucosa. As the mucoadhesive material for forming the adhesive portion, carboxyvinyl polymer, polyacrylic acid and its salts, alginic acid and its salts, adhesive materials such as propylene glycol ester alginate are typical ones. Carboxyvinyl polymer, for example, is commercially available under the trade name of "Carbopol" and "Hiviswako". Mucoadhesive material preferably has a number average molecular weight of 4000 to 6 million.

Mucoadhesive materials used in the present invention is not limited thereto, as long as the adhesive material that can adhere to the mucosa of the body, may be used. The form of the adhesive portion may be a thin layer which is compressed from raw material powder, a film which is molded from raw material, or a coated membrane which is coated and dried from raw material solution.

Mucoadhesive material swells when contacts to the water in the gastrointestinal tract and forms a hydrogel, and the diffusion rate of drug molecules decreases significantly. Therefore, when a mucoadhesive material is contained in the drug layer, or when it is localized over the drug layer to form a layer, absorption rate of the drug will be decreased.

Therefore, the adhesive portion is preferably located on a part of the surface of the drug layer side of the oral preparation.

For example, when the adhesive portion is a hollow cylindrical, located on the outer periphery on the surface of the basal layer and the drug layer is located in the hollow portion of the cylinder, after thus structured oral preparation adheres to the mucosa, the drug layer is surrounded by the mucosa to which oral preparation adheres, by the adhesive portion and by the basal layer. As a result, water such as the surrounding digestive juice is prevented to permeate into the drug layer and drug is prevented to dilute or degradation by hydrolysis or is prevented to diffuse to other site than the mucosa. Further, in such a case, the absorption enhancer and drug is maintained in the same space of the preparation without being diluted, and high concentration gradient of the drug molecules is formed between the absorptive cells and the preparation, the absorption efficiency of the drug becomes high, and particularly preferred.

Figure 4:
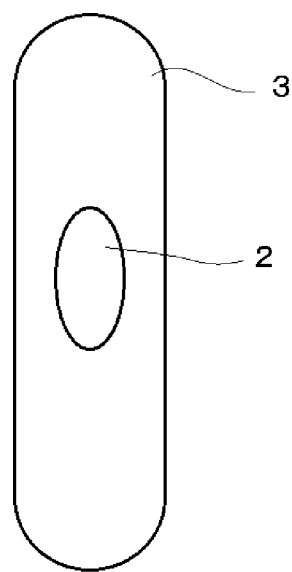

Since the adhesion force of this invented preparation depends on the area of the adhesive portion in contact with the gastrointestinal mucosa, for example, to expand the area of the adhesive portion 3 as shown in FIG. 4, i.e., to relatively increase to the area of the drug layer 2, adhesive force can be increased (C) Drug Layer Drug layer contains a drug that provides pharmacological activity and has the function of releasing it. Drug layer dissolves at the site where the oral preparation adheres, the drug molecules released therefrom is absorbed into the absorptive cells present on the mucosa and delivered to the systemic circulation. Thereafter, they are delivered to the site of action, and exerts pharmacological activity. Drug layer does not contain mucoadhesive materials for the purpose of increasing the absorption rate of the drug. On the other hand, drug layer may contain absorption enhancers and stabilizing agents and the like in addition to the drug.

For example, a surfactant can be used as an absorption enhancer. Surfactants not only accelerate the dissolution of drugs having low solubility but also have a function to increase the bioavailability and pharmacological activity by enhancing the membrane permeability and absorption of low-membrane permeability drugs. Preferred surfactants are glycerol fatty acid esters, sucrose fatty acid esters, calcium stearoyl lactate, sorbitan fatty acid esters, propylene glycol fatty acid esters, polysorbate 80, ethoxylated hydrogenated castor oil, monooleic acid, polyethylene monooleic acid glycol, polyethylene monostearate glycol and medium chain fatty acid triglyceride.

Typical commercial products of surfactants that may be used in the present invention are polyoxyethylene hydrogenated castor oil derivatives HCO-60, CREMOPHOR RH-40 (polyoxyl 40 hydrogenated castor oil), LABRAFIL M 2125 (linoleoyl polyoxyl-6 glycerides) and 1944 (oleoyl polyoxyl-6 glycerides), Polysorbate 80, tocopheroyl TPGS, MIGLYOL 812 (caprylic acid/capric acid triglycerides), CAPMUL MCM (medium chain monoglycerides), CAPMUL PG-8 (propylene glycol caprilyl mono and diglycerides), CREMOPHOR EL (polyoxyl 35 hydrogenated castor oil), LABRASOL (caprilocapyl polyoxy-8 glyceride), TRANS CUTOL P (diethylene glycol monoethyl ether), PLUROL Oleique CC (polyglyceryl-6 dioleic acid ester), LAUROGLYCOL 90 (propylene glycol monolauric acid ester), CAPRYOL 90 (propylene glycol monocaprylic acid), MYVACETS (acetylated monoglycerides), ARLACELS (sorbitan fatty acid esters), PLURONICS (copolymers of propylene and ethylene oxide), BRIJ 30 (polyoxyethylene 4 lauryl ether), GELUCIRE 44/14 (lauroyl polyoxyl-32 glycerides), GELUCIRE 33/01 (glycerol ester of fatty acids), LIPOSORB® P-20 (Lipochem Inc., Patterson N.J.); CAPMUL® POE-0 (Abitec Corp., Janesville, Wis.) and the like.

Absorption enhancers that may be used in the present invention are, for example, capric acid, sodium caprate and its derivatives, for example N-[8-(2-hydroxybenzoyl) amino] caprylic acid (SNAC) and sodium N-[8-(2-hydroxybenzoyl) amino]decanate (SNAD), and organic acids such as citric acid and tartaric acid.

As a further example of absorption enhancers that may be used in the present invention, fatty acids, glycyrrhithin, glycyrrhetinic acid, amino acid enamine derivatives (such as ethyl acetacetate enamin derivatives of phenylglycine), sodium salicylate or derivatives thereof may be cited.

When a drug easily receives hydrolysis by saliva, gastric juice and digestive enzymes, it is possible to obtain a better absorption efficiency of the drug by adding a stabilizing agent. For example, protease inhibitors like casein and lactoferrin derived from natural products are typical stabilizing agents, and show inhibitory effect on the hydrolytic action of digestive enzymes. However, it is not limited to these stabilizing agents.

Preferred stabilizing agents are proteins or pepsin inhibitors. Specific examples of proteins referred to herein are collagen, casein, lactoferrin, albumin and egg white.

As the drugs to which the present invention is particularly desired to be applied, drugs belonging to the following categories are listed up. However, it is not limited to these drugs.

(1) Sleep-Inducing Drugs

Sleep-inducing drugs are the preparations that patients suffering from insomnia just when he needs. In general, many patients cannot satisfy its pharmacological effect when they do not fall asleep within 30 minutes after intake. Specific sleep-inducing agents are triazolam, zopiclone, ezopiclone, zorpidem tartrate, brotisolam, rolmetazepam, lilmazahon hydrochloride hydrate, furnitrazepam, estazolam, nitrazepam, guazepam, haloxazoram, fulazepam hydrochloride, lamertheon, bromovaleryl urea and the like.

(2) Diabetes Therapeutic Drugs

As a drug which is expected to induce hypoglycemic effect rapidly after intake, insulin and its derivatives, and GLP-1 (glucagon-like peptide 1) receptor agonists and the like. In order to suppress the rapid increase in postprandial blood glucose, fast absorption rate and high absorption efficiency after medication is required. As GLP-1 receptor agonists, exenatide, lixenatide, liraglutide, chloraglitide, albigurtide, semaglutide and the like are known.

(3) Anti-Inflammatory Drug

Stomatitis is an inflammation that occurs in the oral mucosa, and the application of anti-inflammatory drugs is effective. However, it is difficult for the applied anti-inflammatory drug to have a long residence time at the inflammatory site because of not only the cleaning action by saliva but also physical activity of the tongue and mouth oral mucosa. By the application of mucoadhesive oral preparation of the present invention composed of three portions to anti-inflammatory drugs, it adheres for a long time to the site of inflammation in the oral cavity, it is possible to maintain a high concentration gradient of anti-inflammatory drugs between the inflammatory site and inside the preparation. It is possible to obtain an excellent pharmacological activity by delivering anti-inflammatory drugs to the site of inflammation with high efficiency. When the mucoadhesive oral preparation of the present invention composed of three portions is used for the oral topical therapy, various steroid drugs and non-steroidal anti-inflammatory drugs are preferable.

(4) Other Drugs, Etc.

As the drugs having poor gastrointestinal mucosal permeability or as the drugs of which activity is decreased by the hydrolysis with digestive enzymes, proteins, peptides, nucleic acids, nucleic acid bases, polysaccharides and the like are listed up. For example, desmopressin, erythropoietin, G-CSF, interferon, and the like low molecular weight heparin may be cited. By applying the mucoadhesive oral preparation of the present invention to these drugs, the possibility of oral dosage form increases because high absorption efficiency from the gastrointestinal mucosa is obtained. Proteins of natural origin easily receive hydrolysis because of low tolerance to the digestive enzymes. However, proteins crosslinked with polyethylene glycol, modified proteins such as glycoproteins, and peptides/proteins substituted with unnatural amino acids are more appropriate drugs to apply the present invention, because they have a resistance to proteases.

The content of the drug as an active component in the oral preparation of the present invention is appropriately adjusted depending on the type and intensity of the desired pharmacological activity. In general, the content of the drug, relative to the oral reparation, is 0.01 to 50 wt %, preferably 0.05 to 40 wt %, more preferably 0.1 to 30 wt %.

Oral preparations of the present invention, for example, can be produced by the following method. That is, at first water-insoluble material is filled at the bottom of the mortar of the tableting machine. Then, the mucoadhesive material is filled along the outer periphery of the mortar, finally a mixture containing a drug and absorption enhancer or optionally stabilizing agent is filled in the central portion of the mortar, a tablet composed of three portions is obtained by pressurizing with a pestle.

Alternatively, at first, mucoadhesive material is filled along the outer periphery of the mortar of the tableting machine. Then, a mixture containing a drug and absorption enhancer or optionally stabilizing agent is filled into the central portion of the mortar of the tableting machine, a tablet composed of two-part configuration is obtained by pressing with a pestle. Thereafter, a tablet composed of three-part is obtained by coating the bottom and the sides of the tablet using the solution of water-insoluble polymer solution such as ethylcellulose and cellulose acetate.

Oral preparations of the present invention is not limited to tablets, it is also possible to take the form of thin film-like preparations. For example, solution in which mucoadhesive materials such as polycarbophil is dissolved is applied in a ring shape on the film of which main component is water-insoluble material such as cellulose acetate. A film preparation having three-part can be produced by applying a drug, absorption enhancer and stabilizing agent etc. in the central portion and drying.

In addition, ring-shaped film made of mucoadhesive material of which central portion was removed is adhered to the film made of water-insoluble material as the main component and drug, absorption enhancer and stabilizing agent etc. are applied in the central hollowed hole portion of the film. Similar film preparation having three-portion can be produced after drying.

The shape and dimensions of the mucoadhesive oral preparation of the present invention is not defined in any way as long as it can be taken orally. For example, if mucoadhesive oral preparation has a dosage form of a tablet, the shape is generally disk-shaped or spheroidal. In that case, the thickness of the disk tablet or spheroidal tablet is 0.5 to 10 mm, preferably 1 to 5 mm, the diameter of the disk tablets is 2 to 20 mm, preferably 5 to 15 mm. The major axis of the spheroidal tablet is 2 to 40 mm, preferably 10 to 30 mm. The minor diameter of the spheroidal tablet is 1 to 20 mm, preferably 7 to 15 mm. Further, if mucoadhesive oral preparation has a dosage form of the film preparation, its thickness is 0.05 to 2 mm, preferably 0.5 to 1 mm.

Further, the mucoadhesive oral preparation of the present invention may have a coating which covers the surface of the drug layer and the adhesive portion and dissolves at the adhered site of the body. For example, when the drug layer or adhesion portion is coated with an enteric coating agent, or when the entire surface of the tablet having a three-portion structure is coated with an enteric coating agent, mucoadhesive oral preparation adheres to the small intestinal mucosa, and it becomes possible to obtain a high absorption efficiency with fast rate from the small intestine.

In the case of so-called multiple-unit system, where a single dose is composed of a plurality of those preparations, individual preparation may be coated with different enteric coating agent, and may be coated with the different mixture of coating agents. In the case of one enteric coating agent, the thickness of the enteric coating of each preparation may differ. In doing so, the problem that the coating layers dissolve at the same site in the gastrointestinal tract and the preparations adhere each other is prevented.

When the target adhering site in the gastrointestinal tract of the mucoadhesive oral preparation of the present invention is assumed to be a wide range, for example, from the upper small intestine to the lower small intestine, the problem can be solved by using several number of mucoadhesive oral preparation of the present invention in one dosing and by using enteric coating agents dissolving at the different small intestinal pHs as the surface membrane. Typical enteric coating agents are hydroxypropyl methylcellulose phthalate (trade name "HPMCP (Hypromellose Phthalate), manufactured by Shinetsu Chemical Industry Co., Ltd.) dissolving at the pH of upper small intestine, methacrylate copolymer (trade name "Eudragit L100], Evonik Rohm GmbH Co., Ltd., Higuchi Shokai Co., Ltd.) dissolving at the pH of middle part of small intestine, and methacrylate copolymer (trade name "Eudragit S100", manufactured by Evonik Rohm GmbH Co., Ltd., Higuchi Shokai sales) dissolving at the pH of lower small intestine. For example, in the case of the treatment with Multiple-unit system having three mucoadhesive oral preparations of the present invention, the problem can be solved by using (1) HPMCP55, (2) Eudragit L100, (3) Eudragit S100 as the surface membrane, respectively. In the case of the therapy with Multiple-unit system having five mucoadhesive oral preparations of the present invention, the problem can be solved using (1) HPMCP55, (2) a mixture of HPMCP55 and Eudragit L100, (3) Eudragit L100, (4) mixture of Eudragit L100 and Eudragit S100, and (5) Eudragit S100 as the surface membrane.

Although the present invention is described more specifically by the following examples, the present invention is not limited by the examples.

Example 1

One hundred mg of cellulose acetate was placed thinly uniformly at the bottom of the mortar, diameter 15 mm, of a tableting machine (Ichihashi Seiki Co., Ltd. single-shot tableting machine "HANDTAB100" (trade name)). The internal shape of the mortar is cylindrical. CBC's carboxyvinyl polymer "Carbopol 974PNF" (trade name, manufacturer Lubrizd Advanced Materials Inc.), 50 mg, was placed along the periphery of the mortar. Carboxymethylcellulose, 93 mg, was uniformly placed in the center of the mortar, thereafter a mixture, 2 mg of nitrazepam and 5 mg of citric acid, was filled. By tableting with a force of about 15 kN, a tablet of the present invention having a disk shape, about 15 mm diameter and about 1 mm thickness, was prepared.

Comparative Example 1

One hundred mg of cellulose acetate was placed thinly uniformly at the bottom of the mortar. Cellulose acetate, 50 mg, was placed along the periphery of the mortar. A mixture, 2 mg of nitrazepam and 5 mg of citric acid, was uniformly filled in the center of the mortar. By tableting with a force of about 15 kN, a tablet of the present invention having a disk shape, about 15 mm diameter and about 1 mm thickness, was prepared.

Example 2

After rinsing the mouth with 100 mL of warm water, the tablets prepared in Example 1 and Comparative Example 1 were attached to the mucosa of the left and right cheeks of the mouth. When the position in the mouth was checked after 30 minutes, the preparation of Example 1 was attached to the same location, but the preparation of Comparative Example 1 moved to another site. After three-days washing out period, the preparation of Example 1 was taken by adhering under the tongue, he slept after about 10 minutes.

Example 3

A mixture of 50 mg of cellulose acetate and 50 mg of hydroxyethylcellulose was uniformly placed at the bottom of the mortar of the tableting machine. 50 mg of Carbopol 974PNF was placed along the periphery of the mortar. A mixture of 2 mg of prednisolone and 98 mg of carboxymethylcellulose was placed uniformly in the center of the mortar. By tableting using a single shot tableting machine, a tablet of the present invention having a disk shape, about 15 mm diameter and about 1 mm thickness, was prepared.

Example 4

A mixture of cellulose acetate, ethylcellulose and monooleate polyoxyethylene sorbitan "polysorbate 80" (manufactured by Nacalai Tesque) was dissolved in a mixture of ethyl acetate and methylene chloride, and was spread on a polytetrafluoroethylene (trade name "Teflon") plate to make a film and shaped into a circle having a diameter of about 1 cm. Viscous solution which was made by dissolving 1 g of Carbopol 974PNF with 10 mL of purified water was applied along the outer periphery of the film at a width of about 3 mm and thereafter dried. After dropping 10 µL of triamcinolone acetonide injective aqueous suspension, 40 mg/mL, to the center and drying, an oral mucosa adhesive oral preparation of the present invention was obtained.

Example 5

100 mg of cellulose acetate was uniformly placed at the bottom of the mortar of the tableting machine. 50 mg of the mixture, Carbopol 974PNF and sodium carbonate (weight ratio 1:1), was placed along the periphery of the mortar. A mixture, 1 mg of insulin, 5 mg of sodium capric acid and 94 mg of carboxymethylcellulose, was placed uniformly in the center of the mortar. A tablet of the present invention having a disk shape, about 15 mm diameter and about 1 mm thickness, was prepared by tableting using a single tableting machine, Comparative Example 2

100 mg of cellulose acetate was uniformly placed at the bottom of the mortar of the tableting machine. Similarly, 50 mg of cellulose acetate was placed along the periphery of the mortar. A mixture of 1 mg of insulin, 5 mg of sodium capric acid and 94 mg of carboxymethylcellulose was placed uniformly in the center of the mortar. By tableting using a single shot tableting machine, a tablet of the present invention having a disk shape, about 15 mm diameter and about 1 mm thickness, was prepared.

Example 6

Adhesion test to the gastric mucosa was carried out using the preparation made in Example 5 and Comparative Example 2. The pig's stomach was cut into 5 cm×5 cm size. Serosal side of the pig's stomach was attached to a fixed stand made of aluminum with surgical Aronalpha. The water-insoluble basal layer side of each preparation made of cellulose acetate was attached to the tip of the Digital Force Gauge FGN-2 (manufactured by Nidec Simpo Co., Ltd.) with double-sided adhesive tape. The force gauge was lowered and stopped at the time when the preparation was contact with the mucosa, where it was contacted for 5 minutes. Thereafter, the force gauge was raised and peeling pressure when the preparation released from the mucosa was measured. As a result, the peeling force of the preparation of Example 5 was 4.3 N and the peeling force of the preparation of Comparative Example 2 was 1.1 N. The preparation having an adhesive portion (Example 5) showed stronger mucoadhesiveness than the preparation having no adhesive portion, Comparative Example 2. Further, the tablets made in Example 5 and Comparative Example 2 were attached to the surface of the pig's stomach for 5 minutes. When they were put into the 200 mL of Japanese Pharmacopoeia dissolution test first solution (pH1.2) and were taken up after soaking for 5 minutes, the preparation of Example 5 was taken out in a state attached to the stomach. But, the preparation of Comparative Example 2 was peeled off from the stomach and dropped into the beaker. The preparation having an adhesive portion (Example 5) showed stronger mucoadhesiveness than the preparation of Comparative Example 2 having no adhesive portion.

Example 7

100 mg of cellulose acetate was placed thinly uniformly at the bottom of the mortar of the tableting machine. 50 mg of Carbopol 974PNF was placed along the periphery of the mortar. Three mL of liraglutide injection preparation (trade name "Victosa") was put into a dialysis tube of which cut-off molecular weight was 2000, dialyzed in 300 mL of pH 8 buffer, and thereafter was freeze-dried. A mixture of thus obtained freeze-dried product, 10 mg of sodium capric acid and 85 mg of hydroxypropylmethylcellulose was placed in the center of the mortar. By tableting using a single shot tableting machine, a tablet of the present invention having a disk shape, about 15 mm diameter and about 1 mm thickness, was prepared.

Example 8

100 mg of cellulose acetate was placed thinly uniformly at the bottom of the mortar of the tableting machine. 50 mg of Carbopol 971P (manufacturer Lubrizd Advanced Materials Inc., sold by CBC) was placed along the periphery of the mortar. A mixture of 1 mg of fluorescein isothiocyanate-labeled insulin (FITC insulin, homemade), 20 mg of sodium capric acid, 35 mg of white sugar and 35 mg of crystalline cellulose, was placed in the center of the mortar. By tableting using a single shot tableting machine, a tablet of the present invention having a disk shape, about 15 mm diameter and about 2 mm thickness, was prepared.

Comparative Example 3

100 mg of cellulose acetate was placed thinly uniformly at the bottom of the mortar of the tableting machine. 50 mg of Carbopol 971P was placed along the periphery of the mortar. A mixture of 1 mg of FITC insulin, 20 mg of sodium capric acid, 17.5 mg of white sugar, 17.5 mg of crystalline cellulose and 35 mg Carbopol 971P was placed in the center of the mortar. By tableting using a single shot tableting machine, a tablet of the present invention having a disk shape, about 15 mm diameter and about 2 mm thickness, was prepared.

Example 9

The permeated amount of drug from the tablets of Example 8 and Comparative Example 3 was measured using a Franz cell for the experiment of in vitro permeability experiment. As the receptor solution, isotonic phosphate buffer, pH 7.4, was used. After the start, samples, 100 microliters, were taken from the receptor solution for 1 hour. The permeated amount of drug into the receptor solution was measured using a HPLC analysis equipment with a fluorescence detector and permeability (%) was measured. Results as shown in Table 1 was obtained.

TABLE 1

| | 5 min | 10 min | 30 min | 60 min |
|---|---|---|---|---|
| Preparation in Example 8 | 8.6 | 31.7 | 67.3 | 86.1 |
| Preparation in Comparative example 3 | 1.3 | 6.7 | 8.1 | 12.2 |

The permeation rate of the drug from the tablet of Comparative Example 3 prepared by formulating a gel-forming adhesive polymer material Carbopol 971P in the drug layer to the receptor solution was slow, only about 12% in one hour. However, the permeation rate of drug from the tablet of Example 8 of the present invention in which adhesive portion was placed along the periphery of the drug layer to the receptor solution was fast, about 90% in 1 hour. Fast permeation and absorption of the drug from the tablets of the present invention were confirmed.

Example 10

After 550 mg of ethylcellulose and 150 mg of triethyl citrate, were dissolved by adding 4 mL of methylene chloride and 1 mL of methanol, and was uniformly spread on a polytetrafluoroethylene (trade name Teflon) plate, a water-insoluble basement membrane was prepared by spreading uniformly thereon to make a circular film of 1.5 cm diameter. A viscous solution was prepared by adding 1 mL of purified water to 50 mg of fluorescein sodium, an ophthalmic diagnostic agent, 50 mf of sodium capric acid and 500 mg of sodium carboxymethylcellulose. Twenty mg of the viscous drug solution was applied on the central portion of the circular basement membrane. The 5% adhesive glue, which was prepared by adding 5 mL of purified water to 2 g of carboxyvinyl polymer "Hiviswako 103" (trade name, manufactured by Fuji Film Wako Pure Chemical Co., Ltd.), and 0.625 g of propylene glycol and kneading, was applied on the periphery of the basement membrane.

Next, enteric surface membrane was prepared on a Teflon plate by spreading 5 mL of methylene chloride and 5 mL of methanol added to dissolve 1.6 g of Eudragit L100 and 100 mg of triethyl citrate. Similarly to the basement membrane, a circular film of which diameter was 1.5 cm was attached on a basement membrane and was degassed and sealed under negative pressure in a vacuum pump to make film preparation. Further, mucoadhesive film preparation of the present invention was made by sealing with concentrated ethylcellulose solution applied on the outer periphery of the film preparation.

Comparative Example 4

A water-insoluble basement membrane was prepared with ethylcellulose as Example 10, and was made to be a circular film of 1.5 cm diameter. A viscous solution was prepared by adding 1 mL of purified water to 50 mg of sodium fluorescein, an ophthalmic diagnostic drug, 50 mg of sodium capric acid and 500 mg of sodium carboxymethylcellulose. 20 mg of viscous drug solution was applied to the central portion of the circular basement membrane. Enteric surface membrane was prepared with Eudragit L100 as in Example 10, and was made to be a film of 1.5 cm diameter as same as basement membrane. After 15% adhesive glue which was prepared by adding 5 mL of purified water to 0.75 g of HivisWako 103 and 0.624 g of propylene glycol and kneading was applied over the whole area of the surface layer membrane, and overlayed on the base membrane, film preparation was made by degassing and sealing under negative pressure in a vacuum pump. Further, concentrated ethylcellulose solution was applied on the outer periphery of the film preparation to seal. Similarly, two kinds of film preparations were made using films of which whole surface were applied with 20% adhesive glue and 40% adhesive glue made of Hiviswako 103, respectively.

Example 11

The permeation rates of drug from the film preparations of Example 10 and Comparative Example 4 to the receptor side was compared using a Franz cell for the experiment of in vitro permeability experiment. As the receptor solution, isotonic phosphate buffer, pH 7.4, was used. After the start, samples, 100 microliters, were collected from the receptor solution for 1 hour. The permeated amount of drug into the receptor solution was measured using a HPLC analysis equipment with a fluorescence detector, and permeability (%) was determined to obtain the results as shown in FIG. 5.

Figure 5:
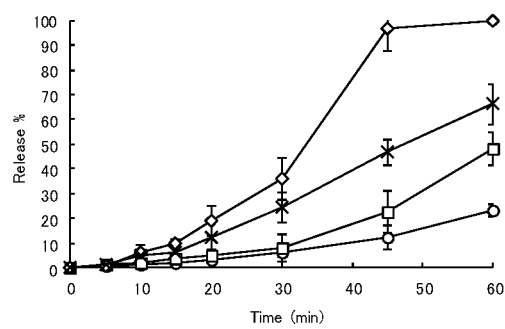

Referring to FIG. 5, the horizontal axis is the elapsed time after the start of the permeation experiment (minutes), and the vertical axis represents the permeability (%). With the film preparation of the present invention of Example 10 (◊ in the figure) where adhesive polymer layer was made on the outer periphery of the film agent, the release rate of the drug was fast, near 100% of drug permeation to the receptor solution was observed within 1 hour. On the other hand, the release rate of the drug from the film preparation of Comparative Example 4 where adhesive polymer layer was made on the whole surface of the surface membrane was significantly decreased. Permeability rate decreased as the content of Hiviswako 103 mucoadhesive polymer material in the adhesive glue increased (15% as to x; 20% as to □; 40% as to ○).

Example 12

50 mg of Carbopol 971P was placed along the periphery of the mortar of the tableting machine. A mixture of 1 mg of sodium fluorescein, 20 mg of sodium capric acid, 35 mg of white sugar and 35 mg of crystalline cellulose was placed in the center of the mortar. By tableting using a single shot tableting machine, a tablet of the present invention having a disk shape, about 15 mm diameter and about 1 mm thickness, was prepared. High-concentration solution prepared by dissolving 500 mg of cellulose acetate and 100 mg of triethyl citrate with 8 mL of acetone was applied on the bottom and sides of the tablet to form a water-insoluble membrane. After drying, enteric coating solution in which 1.6 g of Eudragit L100 and 100 mg of triethyl citrate were dissolved with 8 mL of methylene chloride and 3 mL of methanol was applied on the surface of the tablet. After drying, a tablet of the present invention of about 1 mm thickness was obtained.

Comparative Example 5

50 mg of Carbopol 971P was placed along the periphery of the mortar of the tableting machine. Similar to Example 12, to a mixture of sodium fluorescein, sodium capric acid, white sugar and crystalline cellulose, Carbopol 971P as a mucoadhesive polymer material was added, about 80%, 40% and 10%, and was placed in the center of the mortar. By tableting using a single shot tableting machine, four kinds of tablet of the present invention having a disk shape, about 15 mm diameter and about 1 mm thickness, was prepared. High concentration solution prepared by dissolving 500 mg of cellulose acetate and 100 mg of triethyl citrate with 8 mL of acetone was applied on the bottom and sides of the tablet to form a water-insoluble membrane coating. After dry, enteric coating solution where 1.6 g of Eudragit L100 and 100 mg of triethyl citrate were dissolved with a mixture of 8 mL of methylene chloride and 3 mL of methanol was applied on the surface of the tablet. After dry, four kinds of tablet, about 1 mm thickness, was obtained.

Example 13

The permeation rate of drug from the tablets of Example 12 and Comparative Example 5 to the receptor solution was compared using a Franz cell for in vitro permeability experiment. As the receptor solution, isotonic phosphate buffer, pH 7.4, was used. After the start, samples, 100 microliters, were collected from the receptor solution for 1 hour. The permeated amount of drug into the receptor solution was measured using a HPLC analysis equipment with a fluorescence detector to obtain the results shown in FIG. 6.

Figure 6:
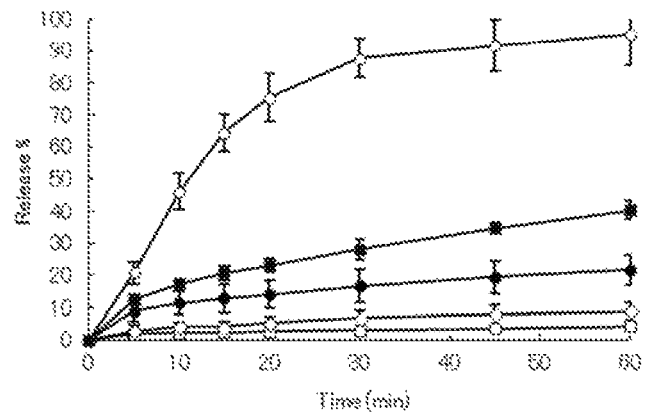

Referring to FIG. 6, the horizontal axis is the elapsed time after the start of the permeation experiment (minutes), and the vertical axis represents the permeability (%). With the tablet of the present invention of Example 12 (○ in the figure) where adhesive polymer material Carbopol 971P layer was made on the outer periphery of the preparation, the release rate of the drug was fast, near 100% of the drug permeation to the receptor solution was observed within 1 hour. On the other hand, the release rate of the drug from the preparation (Comparative Example 5) in which adhesive polymer material Carbopol 971P was formulated in the drug layer was slow. Furthermore, permeability of drug to the receptor solution decreased as the added amount of adhesive polymer material to drug layer was decreased (10% as to ■; 20% as to •; 40% as to ◇; 80% as to □).

Example 14

About 60 mg of a mixture composed of 1 mg of sodium fluorescein, 20 mg of sodium capric acid, 35 mg of white sugar and 35 mg of crystalline cellulose was placed uniformly in the mortar of the tableting machine. 50 mg of Carbopol 971P was placed along the periphery of the mortar of the tableting machine. Then, about 30 mg of a mixture composed of 1 mg of sodium fluorescein, 20 mg of sodium capric acid, 35 mg of white sugar, 30 mg of crystalline cellulose was placed in the center of the mortar. By tableting using a single shot tableting machine, a tablet having a disk shape, about 15 mm diameter and about 1.0 mm thickness, was prepared. High concentration solution prepared by dissolving 500 mg of cellulose acetate and 100 mf of triethyl citrate with 8 mL of acetone was applied on the bottom and sides of the tablet to form a water-insoluble membrane coating. After dry, enteric coating solution in which 1.6 g of Eudragit L100 and 100 mg of triethyl citrate were dissolved with a mixture of 8 mL of methylene chloride and 3 mL of methanol was applied on the surface of the tablet. After dry, a tablet of the present invention of which thickness was about 1 mm was obtained.

Example 15

About a mixture composed of 1 mg of sodium fluorescein, 20 mg of sodium capric acid, 35 mg of white sugar and 35 mg of crystalline cellulose was placed in the mortar of the tableting machine. By tableting using a single shot tableting machine, a tablet, about 15 mm diameter and about 1.0 mm thickness, was prepared. Adhesive glue, which was made by adding 20 mL of purified water to 8 g of Hiviswako103 and 2.5 g of polyethylene glycol 400 and kneading, was applied on the whole surface of the basement membrane, 20 mm diameter, made of cellulose acetate and the tablet was put on the center of the film. Enteric surface membrane was made with Eudragit L100 and was adhered to the base membrane and film preparation was obtained after degassing and sealing under negative pressure by vacuum pump. Furthermore, the outer periphery of the film preparation was applied with cellulose acetate solution to completely seal and the film preparation of the present invention was obtained.

Example 16

200 mg of Hiviswako 103 was filled in a tableting mortar corresponding to the shape of the commercially available size 000 capsule, about 9.5 mm outer diameter and about 26 mm length. Next, a mixture composed of 10 mg of sodium fluorescein, 100 mg of sodium capric acid, 30 mg of white sugar and 30 mg of crystalline cellulose was placed to form two lines as shown in FIG. 3. By tableting using a single shot tableting machine, a tablet having a capsule shape, about 9.5 mm outer diameter, about 26 mm length and about 1.0 mm thickness, was prepared. Then, base membrane was made by applying ethylcellulose solution on the bottom and sides of the tablet and coating with the water-insoluble membrane coating. After dry, a tablet of the present invention, about 1 mm thickness, was obtained by applying with Eudragit L100 enteric coating solution on the surface of the tablet.

INDUSTRIAL APPLICABILITY

In the present invention, by using DDS technology, preparation having a three-portion configuration, it has become possible to develop oral preparation and/or topically applicable oral preparation for oral diseases having increased rate and extent of drug absorption.

DESCRIPTION OF THE REFERENCE NUMBERS

1 . . . Basal layer,
2 . . . Drug layer,
3 . . . Adhesion part.

The invention claimed is:

1. A mucoadhesive oral preparation in a capsule shape having a larger length than width, and having (a) a basal layer substantially consisting of water-insoluble material, (b) a drug layer locating above the basal layer and containing a drug but not containing mucoadhesive material, and (c) an adhesive portion locating on an outer periphery and at the surface of the drug layer side of the oral preparation and containing mucoadhesive material,
wherein an area of the adhesive portion (c) is larger than an area of the drug layer (b).

2. The mucoadhesive oral preparation according to claim 1, wherein the adhesive portion locates on the outer periphery on the surface of the drug layer side of the basal layer, and the drug layer locates in the central portion on the surface of the drug layer side of the basal layer.

3. The mucoadhesive oral preparation according to claim 1, wherein the adhesive portion is substantially consisting of mucosal adherent material.

4. The oral preparation according to claim 1, wherein the water-insoluble material is at least one selected from the group consisting of ethylcellulose, cellulose acetate, chitin, chitosan, aminoalkyl methacrylate copolymer RS, carboxymethylethylcellulose, crystalline cellulose, dimethylaminoethyl methacrylate-methyl methacrylate copolymer, hydroxypropyl starch, hydroxypropyl methylcellulose phthalate, polyvinylacetal diethylaminoacetate, cellulose acetate phthalate, stearic acid, magnesium stearate, acetylglycerol fatty acid ester, magnesium silicate, cholesterol and water-insoluble glycerol fatty acid esters.

5. The oral preparation according to claim 1, wherein the mucoadhesive material is at least one selected from the group consisting of carboxyvinyl polymer, polyacrylic acid and its salts, alginic acid and its salts and propylene glycol alginate ester.

6. The oral preparation according to claim 1, which is a tablet in the capsule shape, and wherein the drug is at least one selected from the group consisting of insulin and insulin derivatives, GLP-1 receptor agonists, sleep inductors, steroids, and anti-inflammatory drug.

7. The oral preparation according to claim 1, which is a film agent in the capsule shape, and wherein the drug is at least one selected from the group consisting of insulin and insulin derivatives, GLP-1 passive agonists, sleep inducers, steroids, and anti-inflammatory drug.

* * * * *